United States Patent [19]

Schulte-Elte et al.

[11] 4,443,632
[45] Apr. 17, 1984

[54] MACROCYCLIC CARBONYL COMPOUNDS, PROCESS FOR THEIR PREPARATION AND THEIR USE AS STARTING MATERIALS FOR THE PREPARATION OF BICYCLIC UNSATURATED HYDROCARBONS

[75] Inventors: Karl H. Schulte-Elte, Onex; Bernard L. Muller, Geneva; Eric Maillefer, Mont-sur-Rolle, all of Switzerland

[73] Assignee: Firmenich SA, Geneva, Switzerland

[21] Appl. No.: 390,808

[22] Filed: Jun. 22, 1982

[30] Foreign Application Priority Data

Jul. 17, 1981 [CH] Switzerland ............... 4708/81

[51] Int. Cl.³ .................. C07C 49/523; C07C 45/61
[52] U.S. Cl. .................... 568/375; 568/445; 585/357
[58] Field of Search ............. 568/445, 375; 585/357

[56] References Cited

U.S. PATENT DOCUMENTS 3,904,651 9/1975 Becker ..................... 568/375 X
4,328,383 5/1982 Eschenmoser et al. ......... 585/357

*Primary Examiner*—Bernard Helfin
*Attorney, Agent, or Firm*—Pennie & Edmonds

[57] ABSTRACT

Compounds of formula

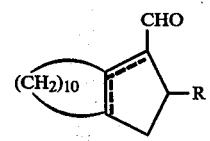

(II)

having a double bond in one of the positions indicated by the dotted lines and wherein R represents a hydrogen atom or a methyl radical are utilized as starting materials for the preparation of bicyclic unsaturated hydrocarbons of formula

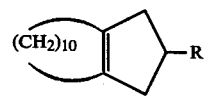

(I)

($R=H$, $CH_3$).

Conversion of (II) to (I) occurs via thermal treatment in the presence of a metal catalyst.

Disclosed is also a process for the preparation of (II).

6 Claims, No Drawings

MACROCYCLIC CARBONYL COMPOUNDS, PROCESS FOR THEIR PREPARATION AND THEIR USE AS STARTING MATERIALS FOR THE PREPARATION OF BICYCLIC UNSATURATED HYDROCARBONS

BRIEF SUMMARY OF THE INVENTION

The present invention relates to novel macrocyclic carbonyl compounds of formula

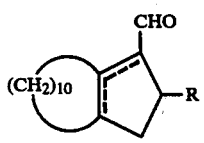
(II)

having a double bond in one of the positions indicated by the dotted lines and wherein R represents a hydrogen atom or a methyl radical.

The invention provides a process for their conversion into compounds of formula

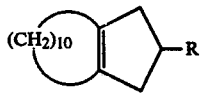
(I)

said process being characterized by a thermal treatment of (II) in the presence of a metal catalyst.

This invention provides further a process for the preparation of compounds (II) starting from an aldehyde of formula

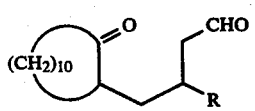
(III)

BACKGROUND OF THE INVENTION

EXALTONE® (Trade Mark of Firmenich SA, Geneva) and muscone are two macrocyclic ketones of great renown within the perfume industry. Their preparation has been the object of various publications reported in several scientific journals [see e.g. J. Chem. Soc. 1964, 4154; Tetrahedron 20, 2601 (1964); Helv. Chim. Acta 50, 708 (1967)].

All those methods however suffer from serious drawbacks whenever one tries to apply them to large scale production, either in view of their complexity or in consideration of the poor yields achieved in certain of the key steps.

One of the known methods [see Helv. Chim. Acta, 50, 705 (1967)] makes use of a compound of formula

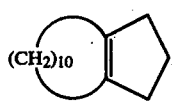
(Ia)

(R=H in formula I) as critical intermediate for the synthesis of EXALTONE®, and of its methylated homologue of formula

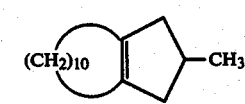
(Ib)

(R=CH$_3$ in formula I) for the preparation of muscone. Both these compounds are obtained from cyclododecanone via a cumbersome process comprising condensation, cyclization, hydrogenation and dehydrogenation. This is indeed a far too complex method for the economical preparation of the desired macrocyclic ketones.

THE INVENTION

The instant invention which is based on a novel and original synthetic approach, presents major advantages over the prior known methods.

According to the invention compounds of formula (II), useful as intermediate compounds for the synthesis of unsaturated hydrocarbons (I), can be easily prepared starting from the compounds of formula

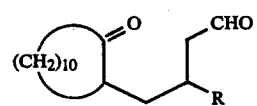
(III)

(R=H, CH$_3$) by subsequently treating them with a base and an acidic agent.

Suitable bases include a mineral or an organic base, for instance a secondary aliphatic or cycloaliphatic amine such as diethyl- or diisopropylamine, piperidine, morpholine or pyrrolidine, in the presence of an organic solvent, e.g. diethyl ether, diisopropyl ether, tetrahydrofuran, dioxan or methylene chloride. Piperidine in the presence of diethyl ether is preferred.

The subsequent treatment with an acidic agent is effected by means of a carboxylic acid, preferably of acetic or propionic acid in admixture with a solvent chosen within the class of solvents cited above, for instance diethyl ether. The cited basic and acidic treatments are carried out at a temperature of between about 0° and 60° C., preferably however in the vicinity of the boiling point of the chosen solvent.

The product resulting from the described reactions consists in a mixture of isomeric bicyclic carbonyl compounds of formulae

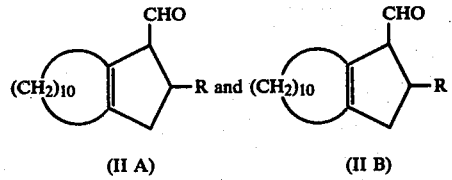

(II A)  (II B)

(R=H, CH$_3$), which isomers can be separated by means of the usual techniques. Such a separation is not always necessary as the subsequent conversion into compounds (I) can advantageously be effected on mixture (II A/II B) as directly obtained by the described process.

According to the invention, compounds (II) can be converted into the desired compounds (I) by thermal treatments in the presence of a metal catalyst. Typically, suitable metal catalysts include metals such as palladium, nickel, platinum, rhodium and cobalt, more often deposited on an inert carrier or support. For practical and economical reasons, palladium over charcoal is preferably utilized.

The said thermal treatment is effected at a temperature which is dependent on the activity of the chosen catalyst. This temperature should anyhow be of at least 150° C. If palladium over charcoal is used, good yields of the end products are achieved by operating at a temperature of about 200° and 210° C. The product recovered in the above said thermal treatment can be converted into EXALTONE® and muscone, respectively, according to known described processes.

Carbonyl compounds of formula (III) used as starting materials for the preparation of compounds (II) according to the invention, are novel chemical entities. They can be synthesized from allyl amd methallyl-cyclododecanone, respectively, by hydroformylation in accordance with the hereinbelow reaction scheme:

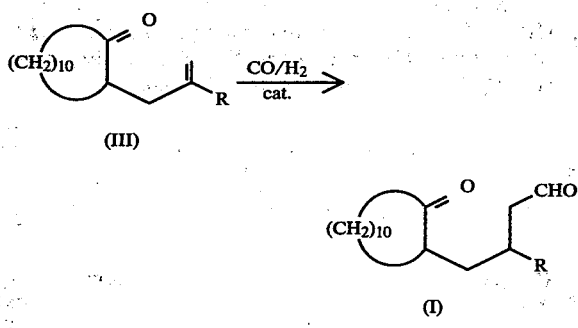

(R=H, CH$_3$). The conditions applied for such a hydroformylation are analogous to those described in the literature for this type of reaction.

The invention will be illustrated in a more detailed manner by the following examples wherein the temperatures are given in degrees centigrade.

EXAMPLE 1

2-(2-Methyl-3-formyl-propyl)-cyclododecanone 150 g (0.63 M) of methallyl-cyclododecanone—Chem. Comm. 1976, 1021—in admixture with 150 ml of cyclohexane and 0.25 g of rhodium hydridocarbonyl-tris (triphenyl-phosphine) were placed into a steel autoclave, and kept stirring during 20 h at room temperature under an atmosphere of CO/H$_2$ (1:1) at a pressure of 150–190×10$^5$ Pa. After fractional distillation of the resulting mixture at about 1 Pa and purification of the obtained residue by chromatography on a silica gel column (eluant:hexane/ether 9:1), there was isolated the desired product with a yield of 75%.

B.p. 80°–100°/10 Pa (Leybold type apparatus).

IR: 2725, 1725, 1720 cm$^{-1}$;

NMR: 0.98 (3H, d, J=7 Hz); 1.3 (18H, m); 9.77 (1H, m) δ ppm;

MS: m/e=236 (15), 221 (5), 204 (24), 189 (15), 178 (40), 163 (50), 135 (28), 123 (75), 107 (40), 99 (100), 81 (30), 69 (35), 45 (46).

EXAMPLE 2

Preparation of
13-formyl-14-methyl-bicyclo[10.3.0]pentadec-12-ene (IIA) and
13-formyl-14-methyl-bicyclo[10.3.0]pentadec-1(12)-ene (IIB)

6.53 g (0.077 M) of freshly distilled piperidine have been added within 20 minutes to 18.6 g (0.07 M) of the compound obtained according to Example 1, in solution in 50 ml of anhydrous ethyl ether at 0°. The reaction mixture was kept under stirring at 0° during one night whereupon ether was added thereto. After washing with two fractions of 100 ml each of brine, drying over Na$_2$SO$_4$ and concentration under reduced pressure, the organic phase gave a residue which was dissolved in 200 ml of anhydrous ether in a nitrogen atmosphere. 9.3 g of glacial acetic acid were added dropwise over 30 min. to the obtained solution and the mixture was brought to reflux for 6 hours. Upon dilution with ether, washing with two fractions of 100 ml each of aqueous NaHCO$_3$ and brine until neutrality, drying over Na$_2$SO$_4$ and evaporation at 6 Pa, there were obtained 14.5 g (yield 83%) of a distillate containing desired products IIA and IIB in a weight ratio of about 2:3.

After separation by vapour phase chromatography (CARBOWAX column), each of compounds IIA and IIB were characterized as follows:

13-formyl-14-methyl-bicyclo[10.3.0]pentadec-12-ene (IIA)

IR: 2745, 1705, 1680, 1660, 1612 cm$^{-1}$;

NMR: 1.08 (3H, d, J=7 Hz); 1.18 (3H, d, J=7 Hz); 1.36 (18H, m); 10.0 (1H, s) δ ppm;

MS: M$^+$=248 (100); m/e=234 (4), 219 (45), 177 (7), 163 (12), 149 (15), 137 (17), 124 (85), 109 (33), 95 (45), 81 (50), 67 (30), 35 (30), 41 (60).

13-formyl-14-methyl-bicyclo[10.3.0]pentadec-1(12)-ene (IIB)

IR: 2700, 1725 cm$^{-1}$;

NMR: 1.10 (3H, d, J=6 Hz), 1.3 (18H, m); 3.0 (1H, m); 9.45 (1H, d, J=4 Hz) δ ppm;

MS: m/e=236 (2), 219 (74), 203 (9), 175 (5), 161 (14), 147 (27), 133 (24), 119 (40), 107 (51), 94 (100), 91 (43), 81 (35), 67 (21), 55 (26), 41 (38), 29 (27).

EXAMPLE 3

Preparation of
14-methyl-bicyclo[10.3.0]pentadec-1(12)-ene 12.4 g of the mixture of compounds obtained in accordance with Example 2 above (purity about 70%) were heated at 200°–210° in the presence of 0.5 g of 10% palladium on charcoal under a pressure of 33×10$^3$ Pa, until the evolution of gas ceased (about 60 min.). By distillation of the obtained residue at 1.73×10$^3$ Pa there was obtained the desired product with a yield of 77%.

An analytical sample of this product was identical in all respects with that prepared in accordance with a prior known literature method.

What we claim is:

1. A compound of formula

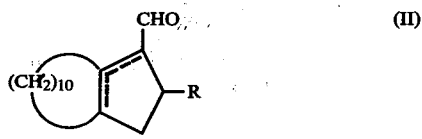

having a double bond in one of the positions indicated by the dotted lines and wherein symbol R designates a hydrogen atom or a methyl radical.

2. 13-Formyl-14-methyl-bicyclo[10.3.0]pentadec-12-ene.

3. 13-Formyl-14-methyl-bicyclo[10.3.0]pentadec-1(12)-ene.

4. Process for the preparation of a compound of formula

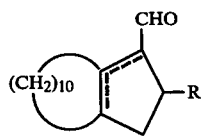
(II)

having a double bond in one of the positions indicated by the dotted lines and wherein R represents a hydrogen atom or a methyl radical, which comprises successively treating with a a secondary aliphatic or cycloaliphatic amine and a carboxylic acid a carbonyl compound of formula

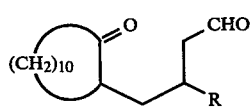
(III)

wherein symbol R is defined above.

5. Process for the preparation of compounds of formula (I)

wherein symbol R represents a hydrogen atom or a methyl radical, which comprises subjecting a compound of formula (II), as defined in claim 1, to a temperature equal to or higher than 150° C. in the presence of a metal catalyst selected from the group consisting of palladium, nickel, platinum, rhodium and cobalt.

6. A compound of formula

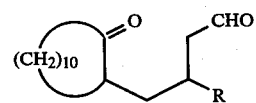
(III)

* * * * *